United States Patent
Dale et al.

(10) Patent No.: US 12,319,899 B1
(45) Date of Patent: Jun. 3, 2025

(54) BEVERAGE ADDITIVE

(71) Applicants: Robert Dale, Culver, OR (US); Lifen Huang So, Culver, OR (US); Timothy Riddle, Appleton, WI (US)

(72) Inventors: Robert Dale, Culver, OR (US); Lifen Huang So, Culver, OR (US); Timothy Riddle, Appleton, WI (US)

(*) Notice: Subject to any disclaimer, the term of this patent is extended or adjusted under 35 U.S.C. 154(b) by 0 days.

(21) Appl. No.: 18/243,074

(22) Filed: Sep. 6, 2023

Related U.S. Application Data

(60) Provisional application No. 63/404,071, filed on Sep. 6, 2022.

(51) Int. Cl.

| | |
|---|---|
| *C12G 3/055* | (2019.01) |
| *A61K 31/00* | (2006.01) |
| *A61K 31/01* | (2006.01) |
| *A61K 31/015* | (2006.01) |
| *A61K 31/047* | (2006.01) |
| *A61K 31/05* | (2006.01) |
| *A61K 31/121* | (2006.01) |
| *A61K 31/122* | (2006.01) |
| *A61K 31/231* | (2006.01) |
| *A61K 31/352* | (2006.01) |
| *A61K 36/185* | (2006.01) |
| *C12G 3/06* | (2006.01) |

(52) U.S. Cl.
CPC .............. *C12G 3/055* (2019.02); *A61K 31/01* (2013.01); *A61K 31/015* (2013.01); *A61K 31/047* (2013.01); *A61K 31/05* (2013.01); *A61K 31/121* (2013.01); *A61K 31/122* (2013.01); *A61K 31/231* (2013.01); *A61K 31/352* (2013.01); *A61K 31/658* (2023.05); *A61K 36/185* (2013.01); *C12G 3/06* (2013.01); *A61K 2236/53* (2013.01)

(58) Field of Classification Search
CPC ........ C12G 3/055; C12G 3/06; A61K 31/658; A61K 31/01; A61K 31/015; A61K 31/047; A61K 31/05; A61K 36/185; A61K 2236/53

USPC ........................................................... 426/536
See application file for complete search history.

(56) References Cited

U.S. PATENT DOCUMENTS

| | | | | |
|---|---|---|---|---|
| 5,965,780 A | * | 10/1999 | Savina | C12F 3/10 568/810 |
| 2003/0014799 P1 | * | 1/2003 | Kumar | A01H 5/02 Plt./324 |
| 2005/0145711 A1 | * | 7/2005 | Blondeau | A61L 9/12 239/60 |
| 2014/0271940 A1 | * | 9/2014 | Wurzer | A61P 25/00 424/725 |

FOREIGN PATENT DOCUMENTS

| | | | | |
|---|---|---|---|---|
| WO | 2019195943 | * | 1/2019 | ........... A61K 36/185 |

OTHER PUBLICATIONS

Maggi, et al., Valorizaiton of CBD-hemp through distallation to provide essential oil and improved cannabinoids profile, Scientific Reports, (2021) 11:19890 (Maggi).*
Gupta, The Total Synthesis of alpha and beta bourbonene, Journal of the American Chemical Society, 90:22, Oct. 23, 1968.*
Terpenes and Cannabinoids Yields and Profile from Direct-Seeded and Transplanted CBD—*Cannabis sativa*, Valtcho D. Zheljazkov, Jay S. Noller, Filippo Maggi, and Robert Dale, Journal of Agricultural and Food Chemistry 2022 70 (34), 10417-10428.

* cited by examiner

*Primary Examiner* — Nikki H. Dees
*Assistant Examiner* — Philip A Dubois
(74) *Attorney, Agent, or Firm* — Intellectual Property Consulting, LLC; Mark N. Melasky; Jared K. Rovira

(57) ABSTRACT

In accordance with embodiments of the invention, a beverage additive is provided. The beverage additive includes β myrcene, β caryophyllene, a Pinene, 5 limonene, and α humulene. In one embodiment, the β myrcene is 3303000 ppm, the β caryophyllene is 1799000 ppm, the α Pinene is 574000 ppm, the 5 limonene is 505000 ppm, and the α humulene is 35000 ppm. A method for infusing a liquor is provided. The method includes the steps of steam distilling a hemp biomass for period of time to extract essential oils, providing a liquor, and adding the extracted essential as a beverage additive oils to said liquor.

10 Claims, No Drawings

BEVERAGE ADDITIVE

CROSS-REFERENCE TO RELATED APPLICATIONS

This application claims priority to U.S. Provisional Patent Application Ser. No. 63/404,071, filed Sep. 6, 2022, the entirety of which is incorporated by reference as if fully disclosed herein.

BACKGROUND OF THE INVENTION

Field of the Invention

The present invention relates generally to formulations made of essential oils for infusing beverages such as distilled spirits, alcoholic beverages, energy beverages, tonics and flavored waters.

General Background

Beverages, such as alcoholic beverages, are frequently mixed with ingredients to modify flavor profiles. With the prevalence of hemp, novel uses of hemp biomass are needed to provide applications for hemp to avoid waste. Because hemp contains numerous terpenes, essential oils, and flavonoids, an application for hemp is to extract essential oils for use in modifying the flavor profile of various spirits. Accordingly, what is needed is method of extracting essential oils from hemp and formulations of essential oils to enhance the flavor and drinkability of a spirit.

SUMMARY OF THE INVENTION

In accordance with embodiments of the invention, a beverage additive is provided. The beverage additive includes β-myrcene, β-caryophyllene, α-pinene, limonene, and α-humulene. In one embodiment, the β-myrcene is 0.33 ppm, the β-caryophyllene is 0.17 ppm, the α-pinene is 0.57 ppm, the limonene is 0.5 ppm, and the α-humulene is 0.35 ppm.

In accordance with embodiments of the invention, a method for infusing a liquor is provided. The method includes a first step of steam distilling a hemp biomass at a temperature of between 165° and 255° for period of time to extract essential oils. The method includes a second step of providing a liquor between 50 and 100 proof. The method includes a third step of adding the extracted essential oils to the liquor. The steam distilling of the hemp biomass eliminates and/or isolates to less than 0.001 ppm of tetrahydrocannabinol (THC), CBD, CBG, CBC, CBVD, CBM, Delta 8 or any psychoactive compounds from the hemp biomass. In one embodiment of the method, the extracted essential oils are β-myrcene, β-caryophyllene, α-pinene, limonene, and α-humulene. In one embodiment of the method, the β-myrcene is 0.33 ppm, the β-caryophyllene is 0.17 ppm, the α-pinene is 0.57 ppm, the limonene is 0.5 ppm, and the α-humulene is 0.35 ppm.

DETAILED DESCRIPTION

It will be readily understood that the components could be arranged and designed in a wide variety of different configurations or be entirely separate. The following more detailed description of the embodiments of the system and method of the disclosure is not intended to limit the scope of the disclosure, as claimed, but is merely representative of possible embodiments of the disclosure.

In accordance with embodiments of the invention, an essential oil beverage additive 100 is provided. The beverage additive 100 comprises β-myrcene, β-caryophyllene, α-pinene, limonene, and α-humulene. In one embodiment, the beverage additive 100 comprises β-myrcene 0.33 ppm, β-caryophyllene 0.17 ppm, α-pinene 0.57 ppm, 0.5 ppm limonene, and 0.35 ppm α-humulene. In one embodiment, the beverage additive 100 is incorporated into an alcoholic beverage, such as gin, vodka, whiskey, rum, bourbon, or any other spirit, or a beer or seltzer, for example. In an exemplary formulation of an alcoholic beverage, 1000 mL of 190 proof distilled filtered gin is mixed with 350.00 mL to 758.7 mL of carbon microfiltered water and 0.017 ppm to 1001.1423 ppm of beverage additive 100. Flavonoids, such as one or more terpenes, may be added to modify the flavor profile. The beverage additive 100 may be extracted from a biomass 102, such as hemp. The biomass 102 may include seeds, stems, and flowers of a hemp plant.

Embodiments of the invention include use of botanicals, such as hemp, and steam distilled extraction of essential oils from hemp seed and/or the steam distilled extraction of essential oil of both the hemp seed and hemp stems for infusion into a distilled spirit, alcoholic beverage, and/or energy beverage. As used herein, an energy beverage is a beverage that contains a stimulant ingredient, such as caffeine or taurine, for example. Distilled essential oils include a primary essential oil group of mono/sesquiterpene flavonoids and phenolic compounds.

The aromatic properties of the beverage additive 100 from the flavonoid, flavin and phenolic profiles contribute to the taste profile of the beverage additive 100. The beverage additive 100 may be infused into (i) a distilled spirit, such as gin, vodka, rum, bourbon, etc., (ii) wines and beer, (iii) other alcoholic beverages, including beers and seltzers, (iv) energy beverages, (v) tonic and mineral waters, and (vi) sports drinks. An effect of the beverage additive 100 is to provide a smooth flavoring to a drink that might otherwise have a bite or burning sensation, such as drinking a liquor straight.

In accordance with embodiments of the invention, a method 200 for infusing a liquor with the beverage additive 100 is provided. The method 200 includes a first step 202 of steam distilling a hemp biomass at a temperature of between 165° and 255° for period of time to extract essential oils. Exemplary essential oils that can be extracted from a hemp biomass include β-myrcene, β-caryophyllene, α-pinene, limonene, and α-humulene, among others, for example. The beverage additive 100 comprises the essential oils extracted in step 202. The method 200 includes a second step 204 of diluting an alcohol with distilled water to between 50 and 100 proof. The method includes a third step 206 of adding the beverage additive 100 to the distilled alcohol. In one embodiment of the method 200, an additional step 208 is included to additional essential oils to further modify the flavor profile of the alcohol. The additional essential oils in step 208 may be derived from hemp or any other source. A non-exhaustive list of possible additives is included below.

Step 202 of the method 200 is operable to eliminate and/or isolate to less than 0.001 ppm of tetrahydrocannabinol (THC), CBD, CBG, CBC, CBVD, CBM, Delta 8 or any psychoactive compounds from the hemp biomass 102. In one embodiment, the essential oils are extracted by ethanol. In one embodiment, the hemp biomass 102 comprises stems, seeds, and leaves. In one embodiment, the period of time is between 35 minutes and 1 hour and 45 minutes. In one embodiment, a pH range of said essential oils extracted from the hemp biomass 102 is between 5.5 and 8.1. In one embodiment, the essential oils extracted from the hemp biomass 102 are 120 terpenoids and contain flavonoids and flavones. In one embodiment, the essential oils are extracted from said hemp biomass 102 by microwave extraction. In one embodiment, the essential oils are extracted from said hemp biomass 102 by a subzero oxygen extraction process.

When using an ethanol extraction process, essential oils are derived from hemp. Ethanol and oil do not mix and thus the compounds can be extracted. Since ethanol and oil do not mix, the ethanol can be reused. The amount of ethanol that is used will affect which terpenes are extracted from the biomass 102. To extract the oils of the exemplary beverage additive 100, 18-22% of the mixture is oil and the remainder is ethanol. Other factors influencing are pressure, time, and temperature. Extracted oils can be separated by pH value.

An exemplary extraction process is found in Terpenes and Cannabinoids Yields and Profile from Direct-Seeded and Transplanted CBD-*Cannabis sativa*, Valtcho D. Zheljazkov, Jay S. Noller, Filippo Maggi, and Robert Dale, Journal of Agricultural and Food Chemistry 2022 70 (34), 10417-10428, the entirety of which is incorporated by reference as if fully disclosed herein.

Embodiments of the beverage additive 100 include the extraction and use of essential oils and their extracts, which contain the flavonoids, flavins, and phenolic compounds wherein the addition of and in a distilled spirit and/or a distilled spirit, alcoholic beverages, and energy beverages, tonic and mineral waters, and sports drinks, which shall not be limited to their incorporation and/or point of incorporation as it relates to a distinct aroma or taste profile. The addition, extraction of essential oils of hemp seed, stem, and leaf whereas a combination of a particular identifiable botanicals wherein the essential oil may or may not be used in the final product.

Embodiments of the steam distillation process 202 of said process 202 to include a process where hemp biomass 102 is distilled using water as a beginning medium with other volatiles and/or other non-volatile compounds and hemp biomass 102 to extract essential oils. The steam condensate and use of boiling water produces a heated vapor between 176° F. (80° C.) and 265° F. (129.4° C.) to transfer the vapor of the volatile essential botanical oils via a condenser, wherein the vapor is cooled and returned to either a liquid or a solid state while the non-volatile residuals remain behind.

In one embodiment, the process 200 is direct steam distillation which utilizes a starting medium of hemp plant biomass comprising the hemp seed, stems and/or stalks and/or a combination of said matrix. The hemp biomass is contained in a stainless vessel which is generally suspended above the heated water in the stainless steel boiling chamber supported by the stainless metal mesh and/or perforated stainless inlet and filter screen and/or multiple screens.

The use of high pressure steam is subjected through this process which, when applied to the botanical plant bio-mass matrix, begins the release of the essential botanical oils from said seeds, stems, and stalks contained in the hemp biomass. The essential oils pass through said inlet, high pressure steam is continually introduced throughout the biomass material containing essential oils to be extracted. The interaction of the steam with the biomass releases the volatile aromatic and flavonoid compounds from the biomass to convert into both vapor and extracted essential oils.

The vaporized material—the plant biomass compounds contained within said biomass—are subjected through a condenser in which the compounds are separated utilizing both hot and cold water. The vapor is then cooled to a specific temperature and pH at which point said oil and/or oils are transitioned into a liquid form in which the isolated terpenes contained within the specific essential oil and/or oils are extracted for the addition of alcohol, such as gin or vodka, for example, as a botanical flavoring compound, which may be added as a specific flavonoid botanical extracted flavoring, no different than a juniper extracted essential botanical oil.

The aromatic vapor and flavonoid compounds exit from the condenser where said extracts are collected within a separator (chamber). Since oil and water do not mix, the essential oils will flocculate at this juncture. There are certain essential oils that will not flocculate and settle to the bottom.

The use of biopolymer matrix and/or matrices from the extraction of essential oils can be classified depending on the nature of the repeating units which are categorized into three groups: (1) polysaccharides which are made of sugars (e.g., cellulose found in plants), (2) proteins which are made of amino acids, and (3) nucleic acids which are made of nucleotides. As referenced from the extraction of cellulose internal structures obtained within the Hemp plant and leaf.

The method 200 is operable to remove the psychoactive compounds from the hemp biomass 102, including THC (Tetrahydrocannabinol), CBD (Cannabinol), CBG (Cannabinol), CBN (Cannabinol), Delta 8 (Delta 8 Tetrahydrocannabinol), or any of the Delta compounds particulates. Through the steam distillation process the said temperatures, set timing and pH of the hemp bio-mass and the separation of specific botanical oil and/or oils which produce the specific named oils to be extracted for use in alcoholic beverages.

Biopolymers are proteins, starch, cellulose, DNA, RNA, lipids, collagen and carbohydrates. Biopolymers are categorized wherein their properties are recognized as polynucleotides, polypeptides and polysaccharides.

In one embodiment, the use of a biopolymer unit in the beverage additive 100 comprises approximately 0.01 percent (%) to 40.0 percent (%) of an essential oil to be infused in a distilled spirit, alcoholic beverage, energy beverage, tonic, mineral water, or sports drink, for example: approximately 0.01 g/ltr. or 10.011423 parts per million (ppm) to 100 g/ltr or 10014.2303 parts per million (ppm) of beverage additive 100 to beverage.

Additional matrices may be included with biopolymers. Essential oils used may be infused from said matrix composition(s) when infused into a liquid formulation of an ethyl alcohol wherein the additional limited amount of said essential oil may be introduced through the extraction process of essential oils from distilled steamed hemp biomass 102 into the prescribed alcohol product.

An exemplary process for the production uses aqueous distilled ethyl alcohol 170.11 to 195.4 proof and, 89.1 to 97.02 by volume which is continually distilled with the addition of water between 38% and 65% in its intent for a distilled product to become sufficient and allowing the said processes and procedures wherein the incorporation of an infused essential oil. The total distilled product will require a retention pH value between 3.57 and 6.25, which would produce a favorable gin and/or vodka with its unique flavor profile.

An object of the invention is to influence the optimal flavor and aromatic profiles by the addition and infusion of essential oils into a natural grain ethyl alcohol between 38% and 65% by wt. The addition of water between 33% and 55% respectively, and the said addition of an essential oil between 0.01 g/ltr. or 10.11423 parts per million (ppm) to 100 g/ltr. or 100114.2303 parts per million (specific to a desired flavor profile to be employed in and wherein through the further process of distillation would establish the desired alcohol product). In one embodiment, the distilled neutral ethyl grain alcohol was used in and for the distillation process in the infusion of a flavored gin and/or flavored vodka.

The filtration and purification of both identified steam distilled essential oil and/or steam distilled oils, in the use of a said infusion, in a neutral ethyl alcohol distilled gin or vodka and its use in and of a filtered, purified distilled water, whereas both the neutral ethyl alcohol and filtered purified water be critical to producing a marketable flavored gin and/or a flavored vodka.

An object of the invention is detailed in research and development for an alternative in alcoholic beverages, distilled spirits and energy beverages by and for the extraction methodology, formulation, predetermination and preparation of flavor compounds, flavonoids and phenolic compounds which are extracted from the steam distillation of the hemp seed(s) and/or of the steam distillation of both the seed(s) and stem producing essential oils and/or flavor compounds of said essential oils in which their contribution as a flavoring and aromatic ingredient employing their effect on sensory receptors and neural connections for both taste and aroma of the finished product.

In the distillation process of producing a gin alcohol, the addition and blending of ethyl alcohol with water, and the addition of various grains and vegetables such as potatoes, rye, barley, sugars, corn, rice and/or wheat, which may be added in the process of producing a gin alcohol.

A flavored infused gin may include additional ingredients, such as essential oil of lemon, essential oil of lime, essential oil of pineapple, essential oil of raspberry, essential oil of strawberry, essential oil of vanilla, essential oil of orange, essential oil of peach, essential oil of cinnamon, and the use of coated fruits for the infusion of gin.

The incorporation of an essential oil in the infusion process enhances the flavor and aromatic profiles of gin and provides a uniqueness and compliments the original flavor profile of traditional ingredients used to produce gin.

The use of flavonoids belonging to a group of polyphenolic compounds and their subclasses, such as anthocyanidins, flavone-3-ols, flavanols, flavanones isoflavones, and flavanones, extracted from the steam distillation of essential oils from hemp seed and/or hemp seeds and stems may provide additional health and biological attributes. Flavonoids possess a physicochemical contribution and influences as related to neural and metabolic activities as it applies to the taste profiles and aromatic effects to be used in an alcoholic product.

Botanical flavonoids are diverse group of phytonutrients of plant compounds. There are more than 6000 types of flavonoids and their constituents. Flavonoids are important natural occurring molecules belonging to a secondary group of metabolites possessing phenolic structure and a major contributor to color, aroma, and flavor.

Embodiments of the process utilize methodologies in the extraction of the essential oils of the botanical beverage additive 100 (flavonoid and/or flavonoids) produced through steam distillation process and/or sub-zero ethanol extraction. This is achieved by the considerations of the elements; i.e., essential oils and the stated influences of the process and its components employing the technology and/or technological methods, processes and progressions utilizing essential oils, specific ingredients, temperature(s), and vaporization of particulates producing a favorable distilled spirit flavor compound and/or flavor compounds to be added to alcoholic beverages and energy beverages as an extract of said favorable flavoring. Flavonoids/essential oils of botanical origin produced by the process are operable for infusion into distilled spirits, alcoholic beverages and energy beverages.

Embodiments of the invention utilize a natural extraction of botanical essential oils, such as juniper berry, for a flavoring into a beverage, such as gin. The juniper berry is the female seed of the species *Juniper communis*. The juniper berry can be combined with the beverage additive 100 in a distilled spirit, alcoholic beverage, or energy beverage, for example.

The juniper berry is used in the production of gin in conjunction with coriander seeds and angelica root; gin may or may not also contain anise seed, bitter orange peel, lemon peel, cinnamon bark and cassia bark as flavoring compounds.

The alternative and complementary flavor and aroma profiles can be modified using a variety of essential oils. The essential oils listed below represent a non-exhaustive list of potential additives to a beverage infused with the beverage additive 100.

The essential oils of lavender and rose and their aromatic compounds are an important factor wherein its components are of significance of said flavor and distinct aroma profile to spirits, such as gin and vodka, respectively.

The extraction of and use of the beverage additive 100 essential oils and their extracts shall not be limited to their incorporation and/or point of incorporation as it relates to an aroma or taste profile. The addition, infusion and/or combination of specific identifiable botanicals which may be used in a beverage.

Below is a list of essential oils that may be used as flavorings in a beverage also containing the beverage additive 100:

The essential oil of juniper berry: α-pinene (39.12%), sabinene (8.87%), β-pinene (12.86%), myrcene (12.2%), limonene (2.23%), β-caryophyllene (4.41%), α-humulene (1.05%), D-germacrene (4.22%), cadinene (1.25%), β-germacrene (1.34%).

The essential oil of coriander: α-pinene (2.89%), camphene (0.31%), sabinene (0.14%), β-pinene (0.21%), myrcene (0.46%), λ carene (7.9%), α-terpinene (0.22%), linalool 69.31%), camphor (4.03%), Terpinene-4-ol (−0.46%), α-terpinol (0.32%), n-decanal (1.74%), geraniol (2.53%), geranyl (1.44%), β-caryophyllene (0.51%).

The essential oil of angelica root: α-pinene (20.7%), α-thujene (0.05%), Camphene (1.1%), sabinene (6.1%), β-pinene (1.8%), myrcene (4.1%), α-phellandrene (5.7%), δ-3-carene (14.2%), α-terpinene (0.5%), D cymene (3.8%), β-phellandrene (13.2%), limonene (13.2%), Cis β Ocimene (1.4%), trans-ocimene (2.6%), Y terpinene (1.0%), terpinolene (1.250%), p methyl 1-5-dien-8-ol (0.3%), cryptone (0.3%), bornyl acetate (0.4%), B bisabolene (0.3), α-copaene-ol (1.3%).

The essential oil of anise seed: tetrachlorethylene (4.179%), 2 heptanal (2 and E) (2.48%), P anisaldehyde (4.79%), trans-anethole (55.41%), 3,5,5,9 tetramethyl(1h) benzocycloheptene (2.02%), 2-1 propyl-4-methoxyl phenyl (3.09%), 4-methoxyl-2-2 3 methoxyl phenyl ester (1.53%).

The essential oil of bitter orange peel: sabinene (4.8%), limonene (53.07%), α-pinene (3.8%), β-pinene (9.53%), cis-ocimene (0.1%), myrcene (3.3%), allo-ocimene (0.04%), pinene 2 (0.03%), α-thujene (0.05%), gamma terpinene (0.11%), neural (4.70%), geranial (3.33%), 1,8, ocimene (3.38%), linalool (3.70%), borneol (5.57%), α-terpine (0.25%), thymol methyl ether (0.06%), ethyl cinnamate (0.06%), borneol acetate (0.01%), β-caryophyllene (0.13%), germacrene (0.01%).

The essential oil of lemon peel: Δ-3-carene (0.4%), β-phellandrene (0.50%), β-myrcene (3.36%), limonene (87.77%), terpinene (0.06%), terpinolene (0.1350), geranial (0.59%), β-linalool (2.99%), nonaldehyde (0.18%), cis-limonene oxide (0.05%), E limonene oxide (0.12%), β-Citronellol (0.28%), terpin-4-ol (0.24%), α-terpineol (0.51%), α-citral (0.64), α-citral (0.41%), α-farnesene (0.10%), β-farnesene (0.14%), decanal (1.53%).

The essential oil of cinnamon bark: benzenepropronol (0.19%), Cis cinnamaldehyde (0.98%), 2 methyl-3-phenyl propenal (0.30%), trans cinnamaldehyde (87.32%), calamenene (0.35%), cinnamaldehyde diethyl acetate (2.34%), α-methoxy cinnamaldehyde (1.88%), alpha longyi pinene (0.24%), 8 cadinene (0.45%), tiadenol (0.81%), copaene (0.46%), β-turmerone (3.31%), alpha bisabol (3.34%), alpha turmerone (0.38%).

The essential oil of cassia bark: α-pinene (0.25%), camphene (0.10%), β-pinene (0.22%), myrcene (0.10%), α-phellandrene (0.13%), limonene (0.29%), p cymene (1.07%), 1-8-cineole (1.07%), camphor (0.08%), benzaldehyde (1.10%), linalool (0.16%), terpinolene (0.04%), α-humulene (0.15%), Isoborneol (0.27%), borneol (1.27%), α-terpineol (2.05%), carvone (0.34%) 0,2-methylhydroxybenzaldehyde (0.12%), Υ elemene (0.41%), hydro cinnamaldehyde (0.24%), methyl eugenol (0.05%), € cinnamaldehyde (88.50%), eugenol (1.08%), α-muurolol (0.24%), hydro cinnamic acid (0.24%).

The essential oil of fennel seed: α-pinene (1.29%), α-terpineol (4.36%), α-thujone (0.73%), myrcene (0.43%), α-phellandrene (2.73%), fenchone (9.37%), p cymene (0.54%), estragole (3.51%), β-phellandrene (1.66%), β-pinene (2.23%), anethole (75.15%), Linalool (4.47%), methyl eugenol (3.12%), (−) caryophyllene (2.46%), humulene diol (0.72%), 1-8-cineole (11.79%).

The essential oil of caraway seed: α-pinene (0.05%), sabinene (0.08%), β-myrcene (0.17%), n octanal (0.08%), limonene (33.5%), trans β-ocimene (0.06%), Υ terpinene (0.02%), linalool (0.09%), cis limonene oxide (0.11%), trans L limonene oxide (0.11%), cis dihydrocarveol (0.10%), trans dihydrocarveol (0.15%), trans carveol (0.12%), cis carveol (0.09%), Carvone (64.2%), perillaldehyde (0.24%), trans anethole (0.11%), trans β-caryophyllene (0.09%).

The essential oil of licorice: glycyrrhizin (22.7%), glycyrrinhetinic acid (16.4%), gabridin (6.1%), quercetin (1.17%), liquiritigenin (3.1%), iso liquiritigenin (0.122%), formononetin (1.44%), licopyano (2.3%), kanzonyl Y, partocratic β (0.16%), glabridin (1.2%), methylarginine (1.44%).

The essential oil of clove: eugenol (78%), eugenol acetate (1.25%), β-caryophyllene (17.4%), α-humulene (2.1%), β-limonene (0.01%), copamene (0.10%).

The essential oil of Orris Root: hexhydrofarnesylactone (8%), neophtadiene (6%), myristic acid (56%), caproic acid (14.5%), lauric acid (15.42%), α-ironic acid (2.85%). Exemplary formulations utilizing the beverage additive 100 as additives for gin and vodka and addition of essential oil(s):

Example i 1000 ml. 190 proof distilled filtered spirit (e.g., gin or vodka), incorporate 350.00 ml to 758.7 ml. of carbon-microfiltered water, 0.017 ppm to 1001.1423 ppm beverage additive 100 (distilled essential oils β-myrcene 0.33 ppm, β-caryophyllene 0.17 ppm, α-pinene 0.57 ppm, limonene 0.5 ppm, α-humulene 0.35 ppm), carbon-micron filtered sterilized bottled.

Example ii 1000 ml. 190 proof distilled filtered spirit (e.g., gin or vodka), incorporate 350.00 ml to 758.7 ml. of carbon-microfiltered water, 0.017 ppm to 1001.1423 ppm beverage additive 100 (distilled essential oils β-myrcene 0.33 ppm, β-caryophyllene 0.17 ppm, α-pinene 0.57 ppm, limonene 0.5 ppm, α-humulene 0.35 ppm), 0.10 ppm limonene, 0.10 ppm 1,8 cineole, 0.10 ppm terpinene, 0.10 ppm lavandulyl acetate, 0.10 ppm 3 octanone, 0.1000 ppm linalool, 0.10 ppm linalyl acetate, carbon-micron filtered sterilized bottled.

Example iii 1000 ml. 190 proof distilled filtered spirit (e.g., gin or vodka), incorporate 350.00 ml to 758.7 ml. of carbon-microfiltered water, 0.017 ppm to 1001.1423 ppm beverage additive 100 (distilled essential oils β-myrcene 0.33 ppm, β-caryophyllene 0.17 ppm, α-pinene 0.57 ppm, limonene 0.5 ppm, α-humulene 0.35 ppm), 0.10 ppm limonene, 0.10 ppm 1,8 cineole, 0.10 ppm terpinene, 0.10 ppm lavandulyl acetate, 0.10 ppm 3 octanone, 0.1000 ppm linalool, 0.10 ppm linalyl acetate, 0.10 ppm geraniol, 0.10 Citronellol ppm, Nerol 0.10 ppm, α-rose oxide 0.10 ppm, 0.10 ppm trans rose oxide, 0.10 ppm β phenethyl alcohol, 0.10 ppm farness, 0.10 eugenol.

Example iv 1000 ml. 190 proof distilled filtered spirit (e.g., gin or vodka), incorporate 350.00 ml to 758.7 ml. of carbon-microfiltered water, 0.017 ppm to 1001.1423 ppm beverage additive 100 (distilled essential oils β-myrcene 0.33 ppm, β-caryophyllene 0.17 ppm, α-pinene 0.57 ppm, limonene 0.5 ppm, α-humulene 0.35 ppm), limonene 0.01012 ppm, linalool 0.0013 ppm, rose oxide 0.0111 ppm, Isoborneol 0.0011 ppm, borneol 0.1101 ppm, endo-fenchyl acetate 0.0113 ppm, geraniol 0.1145 ppm, β bourbononene e-caryophyllene 0.1001 ppm, isomethone 0.0004 ppm, carbon-micron filtered sterilized bottled.

Example v 1000 ml. 190 proof distilled filtered spirit (e.g., gin or vodka), incorporate 350.00 ml to 758.7 ml. of carbon-microfiltered water, 0.017 ppm to 1001.1423 ppm beverage additive 100 (distilled essential oils β-myrcene 0.33 ppm, β-caryophyllene 0.17 ppm, α-pinene 0.57 ppm, limonene 0.5 ppm, α-humulene 0.35 ppm), carbon-micron filtered sterilized bottled.

Example vi 1000 ml. 190 proof distilled filtered spirit (e.g., gin or vodka), incorporate 350.00 ml to 758.7 ml. of carbon-microfiltered water, 0.017 ppm to 1001.1423 ppm beverage additive 100 (distilled essential oils β-myrcene 0.33 ppm, β-caryophyllene 0.17 ppm, α-pinene 0.57 ppm, limonene 0.5 ppm, α-humulene 0.35 ppm), 0.10 ppm limonene, 0.10 ppm 1,8 cineole, 0.10 ppm terpinene, 0.10 ppm lavandulyl acetate, 0.10 ppm 3 octanone, 0.1000 ppm linalool, 0.10 ppm linalyl acetate, carbon-micron filtered sterilized bottled.

Example vii 1000 ml. 190 proof distilled filtered spirit (e.g., gin or vodka), incorporate 350.00 ml to 758.7 ml. of carbon-microfiltered water, 0.017 ppm to 1001.1423 ppm beverage additive 100 (distilled essential oils β-myrcene 0.33 ppm, β-caryophyllene 0.17 ppm, α-pinene 0.57 ppm, limonene 0.5 ppm, α-humulene 0.35 ppm), 0.10 ppm limonene, 0.10 ppm 1,8 cineole, 0.10 ppm terpinene, 0.10 ppm lavandulyl acetate, 0.10 ppm 3 octanone, 0.10 ppm linalool, 0.10 ppm linalyl acetate, 0.10 ppm geraniol, 0.10 ppm Citronellol, Nerol 0.10 ppm, α-rose oxide 0.1012 ppm, 0.10 ppm trans rose oxide, 0.10 ppm β phenethyl alcohol, 0.10 ppm farness, 0.10 eugenol.

Example viii 1000 ml. 190 proof distilled filtered spirit (e.g., gin or vodka), incorporate 350.00 ml to 758.7 ml of carbon-microfiltered water, 0.017 ppm to 1001.1423 ppm beverage additive 100 (distilled essential oils β-myrcene 0.33 ppm, β-caryophyllene 0.17 ppm, α-pinene 0.57 ppm, limonene 0.5 ppm, α-humulene 0.35 ppm), carbon-micron filtered sterilized bottled.

The syntax of grammar used herein the singular forms "a", "and", and "the" include plural referents unless the context clearly dictates otherwise. Thus, for example, reference to "compound," "a molecule" includes a plurality of such constituents and reference to "the essential oil" includes reference to one or more botanicals and equivalents thereof known to those skilled in the arts of science, technology, formulation and regulations in food, pharmaceuticals, medicine and health.

All technical and scientific terms used herein have the same meaning as commonly understood to one of ordinary skill in the art to which this invention belongs unless clearly indicated otherwise containing terms; therefore, wherein, said, thus.

The terms "about" or "around" as used herein refer to a margin of 0+ or –% (percent) and/or ppm (parts per million) of the number indicated. For sake of precision, the term "about" when used in conjunction with, for example: 0.001% to a greater than and/or parts per million i.e., from 0.001% to 99.00%. When used in the context of a pH, the term "about" means+/–0.10 pH unit value; as an example, from 7.0 pH to 7.1 pH represents the hydrogen ion concentration of a particulate. This example would represent an increase in alkalinity.

For the purposes of promoting an understanding of the principles of the invention, specific language has been used to describe these embodiments. However, this specific language intends no limitation of the scope of the invention, and the invention should be construed to encompass all embodiments that would normally occur to one of ordinary skill in the art. The particular implementations described herein are illustrative examples of the invention and are not intended to otherwise limit the scope of the invention in any way. For the sake of brevity, conventional aspects of the system (and components of the individual operating components of the system) may not be described in detail. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. A beverage additive, comprising 0.33 ppm β myrcene, 0.17 ppm β caryophyllene, 0.57 ppm α Pinene, 0.5 ppm limonene, and 0.35 ppm α humulene.

2. The beverage additive of claim 1, further comprising 1,8 cineole, terpinene, lavandulyl acetate, 3 octanone, linalool, and linalyl acetate.

3. The beverage additive of claim 1, further comprising 0.10 ppm 1,8 cineole, 0.10 ppm terpinene, 0.10 ppm lavandulyl acetate, 0.10 ppm 3 octanone, 0.1000 ppm linalool, and 0.10 ppm linalyl acetate.

4. The beverage additive of claim 1, further comprising 1,8 cineole, terpinene, lavandulyl acetate, 3 octanone, linalool, linalyl acetate, geraniol, citronellol, Nerol, α rose oxide, trans rose oxide, β phenethyl alcohol, farness, and eugenol.

5. The beverage additive of claim 1, further comprising 0.10 ppm 1,8 cineole, 0.10 ppm terpinene, 0.10 ppm lavandulyl acetate, 0.10 ppm 3 octanone, 0.1000 ppm linalool, 0.10 ppm linalyl acetate, 0.10 ppm geraniol, 0.10 citronellol ppm, 0.10 ppm Nerol, 0.10 ppm α rose oxide, 0.10 ppm trans rose oxide, 0.10 ppm β phenethyl alcohol, 0.10 ppm farness, and 0.10 eugenol.

6. The beverage additive of claim 1, further comprising linalool, rose oxide, Isoborneol, borneol, endo-fenchyl acetate, geraniol, β bourbononene e-caryophyllene, and isomethone.

7. The beverage additive of claim 1 further comprising linalool 0.0013 ppm, rose oxide 0.0111 ppm, Isoborneol 0.0011 ppm, borneol 0.1101 ppm, endo-fenchyl acetate 0.0113 ppm, geraniol 0.1145 ppm, β bourbononene e-caryophyllene 0.1001 ppm, and isomethone 0.0004 ppm.

8. The beverage additive of claim 1, further comprising 0.10 ppm 1,8 cineole, 0.10 ppm terpinene, 0.10 ppm lavandulyl acetate, 0.10 ppm 3 octanone, 0.1000 ppm linalool, and 0.10 ppm linalyl acetate.

9. The beverage additive of claim 1, further comprising 0.10 ppm 1,8 cineole, 0.10 ppm terpinene, 0.10 ppm lavandulyl acetate, 0.10 ppm 3 octanone, 0.10 ppm linalool, 0.10 ppm linalyl acetate, 0.10 ppm geraniol, 0.10 ppm citronellol, Nerol 0.10 ppm, a rose oxide 0.1012 ppm, 0.10 ppm trans rose oxide, 0.10 ppm β phenethyl alcohol, 0.10 ppm farness, and 0.10 eugenol.

10. The beverage additive of claim 1, further comprising: 1000 mL of 190 proof spirit; and 350.00 mL to 758.7 mL of water.

* * * * *